United States Patent [19]

Förster et al.

[11] Patent Number: 4,756,741

[45] Date of Patent: Jul. 12, 1988

[54] AZOLYLOXY-CARBOXYLIC ACID AMIDE COMPOUNDS AND HERBICIDAL COMPOSITIONS

[75] Inventors: Heinz Förster; Wolfgang Hofer; Volker Mues, all of Wuppertal; Ludwig Eue, Leverkusen; Robert R. Schmidt, Cologne, all of Fed. Rep. of Germany

[73] Assignee: Bayer Aktiengesellschaft, Leverkusen, Fed. Rep. of Germany

[21] Appl. No.: 819,200

[22] Filed: Jan. 15, 1986

Related U.S. Application Data

[60] Division of Ser. No. 526,518, Aug. 26, 1983, Pat. No. 4,645,525, which is a continuation of Ser. No. 132,055, Mar. 20, 1980, abandoned.

[30] Foreign Application Priority Data

Apr. 6, 1979 [DE] Fed. Rep. of Germany ....... 2914003
Feb. 6, 1980 [DE] Fed. Rep. of Germany ....... 3004326

[51] Int. Cl.$^4$ .................... A01N 43/78; A01N 43/82
[52] U.S. Cl. ........................ 71/90; 548/129; 548/136; 548/146; 71/88; 71/92
[58] Field of Search ............ 71/118, 90; 548/142, 548/136

[56] References Cited

U.S. PATENT DOCUMENTS

| | | | |
|---|---|---|---|
| 3,414,400 | 12/1968 | Watanabe | 71/118 |
| 3,556,768 | 1/1971 | Inoue et al. | 71/118 |
| 4,120,690 | 10/1978 | Cahoy | 71/90 |
| 4,175,081 | 11/1979 | Driscoll | 71/90 |
| 4,182,712 | 1/1980 | Driscoll | 71/90 |
| 4,388,464 | 6/1983 | Kristinsson et al. | 71/90 |
| 4,528,379 | 7/1985 | Cölln et al. | 548/136 |
| 4,585,471 | 4/1986 | Forster et al. | 71/90 |

*Primary Examiner*—Glennon H. Hollrah
*Assistant Examiner*—A. Owens
*Attorney, Agent, or Firm*—Felfe & Lynch

[57] ABSTRACT

Azolyloxy-carboxylic acid amides of the formula

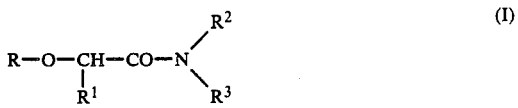

wherein

R is a five-membered hetero-aromatic monocyclic radical which contains an oxygen atom or a sulfur atom and 1 to 3 nitrogen atoms; or R is said monocyclic radical substituted by halogen, nitro, cyano, amino, alkylamino, dialkylamino, arylamino, alkylcarbonylamino, alkylcarbonyl, carboxyl, alkoxycarbonyl, carbamoyl, alkylaminocarbonyl, dialkylaminocarbonyl, arylaminocarbonyl substituted arylaminocarbonyl wherein the substituents are halogen, nitro or alkyl, aryl, substituted aryl wherein the substituents are halogen, nitro, cyano, alkyl, halogenoalkyl or alkoxy, aralkyl, haloaralkyl, alkoxy, halo-alkoxy, alkenoxy, alkynoxy, alkoxycarbonylalkoxy, aralkoxy or aryloxy, optionally halogen-substituted alkylthio, alkenylthio, alkynylthio, alkoxycarbonylalkylthio, aralkylthio, arylthio, alkylsulphinyl or alkylsulphonyl, optionally halogen-substituted alkyl, alkenyl, alkynyl, alkoxyalkyl, aralkoxyalkyl, aryloxyalkyl, alkylthioalkyl, alkylsulphinylalkyl, alkylsulphonylalkyl, arylthioalkyl, arylsulphinylalkyl, arylsulphonylalkyl, carboxyalkyl, alkoxycarbonylalkyl, optionally substituted aminocarbonylalkyl, cyanoalkyl or cycloalkyl, $R^1$ is hydrogen or alkyl and $R^2$ and $R^3$ are individually selected from hydrogen, optionally substituted alkyl, alkenyl, alkynyl, aralkyl, cycloalkyl or aryl, or a nitrogen-containing heterocyclic radical, or $R^2$ and $R^3$, together with the nitrogen atom to which they are bonded, represent an optionally substituted, optionally partially unsaturated and optionally benzofused monocyclic or bicyclic radical which optionally contains one or more further hetero-atoms; are effective herbicides.

15 Claims, No Drawings

AZOLYLOXY-CARBOXYLIC ACID AMIDE COMPOUNDS AND HERBICIDAL COMPOSITIONS

This application is a divisional of application Ser. No. 526,518 filed Aug. 26, 1983, now U.S. Pat. No. 4,645,525 which is a continuation of application Ser. No. 132,055 filed Mar. 20, 1980, now abandoned.

This invention relates to certain new azolyloxy-carboxylic acid amide compounds, to herbicidal compositions containing them and to methods of combating undesired vegetation utilizing such compounds.

It is already known that certain phenoxy-carboxylic acid amides, for example 2,4-dichlorophenoxyacetic acid amide, have a herbicidal action (see French Patent Specification No. 1,313,840). However, the phenoxy-carboxylic acid amides known as herbicides display only a slight action against graminaceous weeds when the customary amounts are applied and, because of their inadequate selectivity, cannot be used for combating broad-leaved weeds in various dicotyledon crops.

The present invention now provides, as new compounds, the azolyloxy-carboxylic acid amides of the general formula

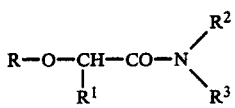
(I)

in which

R represents a five-membered hetero-aromatic monocyclic radical which contains an oxygen atom or a sulphur atom and in addition 1 to 3 nitrogen atoms and which is optionally substituted by halogen, nitro, cyano, amino, alkylamino, dialkylamino, arylamino, alkylcarbonylamino, alkylcarbonyl, carboxyl, alkoxycarbonyl, carbamoyl, alkylaminocarbonyl, dialkylaminocarbonyl, arylaminocarbonyl (which is optionally substituted by halogen, nitro or alkyl), aryl (which is optionally substituted by halogen, nitro, cyano, alkyl, halogenoalkyl or alkoxy), aralkyl (which is optionally substituted by halogen), optionally halogen-substituted alkoxy, alkenoxy, alkynoxy, alkoxycarbonylalkoxy, aralkoxy or aryloxy, optionally halogen-substituted alkylthio, alkenylthio, alkynylthio, alkoxycarbonylalkylthio, aralkylthio, arylthio, alkylsulphinyl or alkylsulphonyl, optionally halogen-substituted alkyl, alkenyl, alkynyl, alkoxyalkyl, aralkoxyalkyl, aryloxyalkyl, alkylthioalkyl, alkylsulphinylalkyl, alkylsulphonylalkyl, arylthioalkyl, arylsulphinylalkyl, arylsulphonylalkyl, carboxyalkyl, alkoxycarbonylalkyl, optionally substituted aminocarbonylalkyl, cyanoalkyl or cycloalkyl, $R^1$ represents hydrogen or alkyl and $R^2$ and $R^3$ are identical or different and individually represent hydrogen, an alkyl, alkenyl, alkynyl, aralkyl, cycloalkyl or aryl radical that is optionally substituted in each case, or a nitrogen-containing heterocyclic radical, or $R^2$ and $R^3$, together with the nitrogen atom to which they are bonded, represent an optionally substituted, optionally partially unsaturated and optionally benzo-fused monocyclic or bicyclic radical which optionally contains one or more further hetero-atoms.

The azolyloxy-carboxylic acid amides of the formula (I) are distinguished by a powerful herbicidal activity.

Preferred compounds according to this invention are those of the general formula

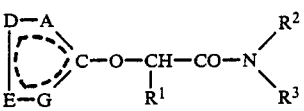
(Ia)

in which

A represents C—$R^4$ or N,

D represents C—$R^5$ or N,

E represents C—$R^6$, N, O or S and

G represents C—$R^7$, N, O or S, with the proviso that at least one of the ring members (A, D, E or G) represents N and at least one of the ring members represents O or S, $R^1$ represents hydrogen or methyl, $R^2$ and $R^3$ are identical or different and individually represent hydrogen, alkyl, cyanoalkyl, alkoxyalkyl, alkylthioalkyl, alkenyl or alkynyl, in each case with up to 10 carbon atoms, cycloalkyl with up to 12 carbon atoms, aralkyl which has 1 or 2 carbon atoms in the alkyl part and 6 or 10 carbon atoms in the aryl part and which is optionally substituted by halogen, or aryl with 6 or 10 carbon atoms, it being possible for the aryl radical to be substituted by 1 to 3 halogen atoms, 1 to 3 alkyl or halogenoalkyl groups with 1 to 4 carbon atoms in each case, nitro, cyano or alkoxy with 1 to 4 carbon atoms, or $R^2$ and $R^3$, together with the nitrogen atom to which they are bonded, form an optionally partially unsaturated and/or benzo-fused monocyclic or bicyclic radical which has up to 15 carbon atoms and is optionally substituted by 1 to 3 alkyl groups with in each case 1 to 5 carbon atoms or by two geminal alkoxy groups with in each case 1 to 3 carbon atoms or is optionally substituted by dioxolanylidene or dioxanylidene radicals linked in a spiro-cyclic manner, or $R^2$ and $R^3$, together with the nitrogen atom to which they are bonded, form a saturated monocyclic radical which has up to 5 carbon atoms, contains a further nitrogen atom, oxygen atom or sulphur atom and is optionally substituted by 1 to 3 alkyl groups with in each case 1 to 5 carbon atoms, by phenyl which is optionally substituted by $C_1$–$C_4$-alkyl, $C_1$–$C_4$-alkoxy, halogen, $C_1$–$C_2$-halogenoalkyl or nitro, or by benzyl or phenylethyl, $R^4$, $R^5$, $R^6$ and $R^7$, which can be identical or different, individually represent hydrogen, halogen, nitro, cyano, amino, $C_1$–$C_4$-alkylamino, di-$C_1$–$C_4$-alkylamino, $C_1$–$C_4$-alkylcarbonylamino, $C_1$–$C_4$-alkyl-carbonyl, carboxyl, $C_1$–$C_4$-alkoxy-carbonyl, carbamoyl, $C_1$–$C_4$-alkylamino-carbonyl, di-$C_1$–$C_4$-alkyl-amino-carbonyl, phenylamino-carbonyl which is optionally substituted by halogen, nitro or $C_1$–$C_4$-alkyl, phenyl which is optionally substituted by halogen, nitro, cyano, $C_1$–$C_4$-alkyl, $C_1$–$C_4$-halogenoalkyl, or $C_1$–$C_4$-alkoxy, optionally halogen-substituted benzyl or phenylethyl, optionally halogen-substituted $C_1$–$C_4$-alkoxy, $C_2$–$C_4$-alkenoxy, $C_2$–$C_4$-alkynoxy, $C_1$–$C_4$-alkoxy-carbonylmethoxy, benzyloxy or phenoxy, optionally halogen-substituted $C_1$–$C_4$-alkylthio, $C_2$–$C_4$-alkenylthio, $C_2$–$C_4$-alkynylthio, $C_1$–$C_4$-alkoxy-carbonyl-methylthio, benzylthio, phenylthio, $C_1$–$C_4$-alkyl-sulphinyl or $C_1$–$C_4$-alkylsulphonyl, optionally halogen-substituted $C_1$–$C_6$-alkyl, $C_2$–$C_6$-alkenyl or $C_2$–$C_6$-alkynyl, cyano-$C_1$–$C_4$-alkyl, $C_1$–$C_4$-alkoxy-$C_1$–$C_2$-alkyl, phenoxy- or phenylthio-methyl, benzyloxy- or benzylthio-methyl, $C_1$–$C_4$-alkylthio-$C_1$–$C_2$-alkyl, $C_1$–$C_4$-alkyl- or phenylsulphinyl-$C_1$–$C_2$-alkyl, $C_1$–$C_4$-alkyl- or phenylsulphonyl-$C_1$–$C_2$-alkyl, carboxy-$C_1$–$C_2$-alkyl, $C_1$–$C_4$-alkoxycarbonyl-$C_1$–$C_2$-alkyl, $C_1$–$C_4$-alkylamino-carbonyl-$C_1$–$C_2$-alkyl, di-$C_1$–$C_4$-alkylamino-carbonyl-$C_1$–$C_2$-alkyl, phenylaminocarbonylalkyl or $C_3$–$C_{12}$-cycloalkyl.

The present invention also provides a process for the preparation of an azolyloxy-carboxylic acid amide of the general formula (I) in which an α-hydroxycarboxylic acid amide of the general formula

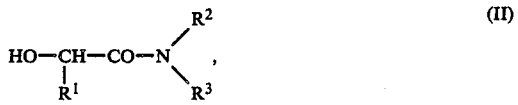

(II)

in which
$R^1$, $R^2$ and $R^3$ have the meanings indicated above, is reacted with a halogenoazole of the general formula R—Hal    (III), wherein
R has the meaning indicated above and
Hal represents chlorine, bromine or iodine, if appropriate in the presence of an acid acceptor and if appropriate using a diluent.

Some of the compounds of the formula (I) can indeed also be synthesised in another manner, for example from the corresponding hydroxy-azoles (or the azolones tautomeric to these compounds) and α-halogenocarboxylic acid amides, or from corresponding azolyloxy-carboxylic acid esters and amines; however, the extent to which these methods can be applied is relatively small.

Surprisingly, the present azolyloxy-carboxylic acid amides exhibit a considerably better herbicidal action, which is of a different type, than the phenoxycarboxylic acid amides known from the state of the art. It is particularly surprising that the compounds according to the invention, which are well tolerated by useful plants, also exhibit a very good action against graminaceous weeds, in addition to their powerful action against dicotyledon weeds, while such structurally similar phenoxyalkanecarboxylic acid derivatives as, for example, 2,4-dichlorophenoxy-acetic acid amide display only a slight action against Gramineae.

The particularly preferred compounds of the formula (I) are those in which
$R^1$ represents hydrogen,
$R^2$ represents hydrogen, $C_1$–$C_5$-alkyl, cyanoethyl, $C_1$–$C_4$-alkoxy-ethyl, allyl, propargyl, 1-methyl-propargyl, 1,1-dimethyl-propargyl, cyclopentyl, cyclohexyl, phenyl or benzyl and
$R^3$ represents $C_1$–$C_5$-alkyl, cyanoethyl, $C_1$–$C_4$-alkoxyethyl, allyl, propargyl, 1-methyl-propargyl, 1,1-dimethylpropargyl, cyclopentyl, cyclohexyl, benzyl, naphthyl or phenyl, which is optionally substituted by 1 to 3 radicals (selected from methyl, fluorine, chlorine, trifluoromethyl, cyano, nitro and methoxy), or
$R^2$ and $R^3$, together with the nitrogen atom to which they are bonded, represent pyrrolidyl, monoalkyl- or dialkyl-pyrrolidyl with 1 to 3 carbon atoms per alkyl group, morpholinyl or dialkylmorpholinyl with 1 to 3 carbon atoms per alkyl group, piperidyl, monoalkyl-, dialkyl- or trialkyl-piperidyl with 1 to 3 carbon atoms per alkyl group, 4,4-dialkoxy-piperidyl with 1 to 3 carbon atoms per alkoxy group, spiro-substituted piperidyl of the general formula

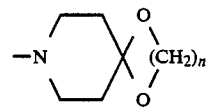

wherein
n represents 2 or 3, perhydroazepinyl (hexamethyleneimino radical), trimethyl-perhydroazepinyl, the heptamethyleneimino radical, the dodecamethyleneimino radical, 1,2,3,4-tetrahydroindolyl, monoalkyl- dialkyl- or trialkyl-1,2,3,4-tetrahydroindolyl with up to 3 carbon atoms per alkyl group, perhydroindolyl, monoalkyl-, dialkyl- or trialkyl-perhydroindolyl with 1 to 3 carbon atoms per alkyl group, 1,2,3,4-tetrahydroquinolyl or 1,2,3,4-tetrahydro-isoquinolyl, monoalkyl-, dialkyl- or trialkyl-1,2,3,4-tetrahydro-quinolyl or -isoquinolyl with 1 to 3 carbon atoms per alkyl group, perhydroquinolyl or perhydro-isoquinolyl, monoalkyl-, dialkyl- or trialkyl-perhydroquinolyl or -perhydroisoquinolyl with 1 to 3 carbon atoms per alkyl group, perhydrothiazolyl, perhydrooxazolyl, perhydrooxazinyl or a radical of the general formula

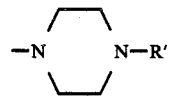

wherein
R′ represents $C_1$–$C_4$-alkyl, phenyl (which optionally carries one or more substituents selected from $C_1$–$C_2$-alkyl, $C_1$–$C_2$-alkoxy, fluorine, chlorine, bromine, trifluoromethyl and or nitro), benzyl or phenylethyl, or
$R^2$ and $R^3$, together with the nitrogen atom to which they are bonded, represent the radical

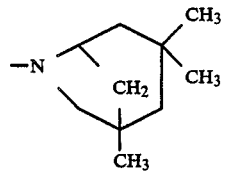

and
R represents one of the azolyl radicals below

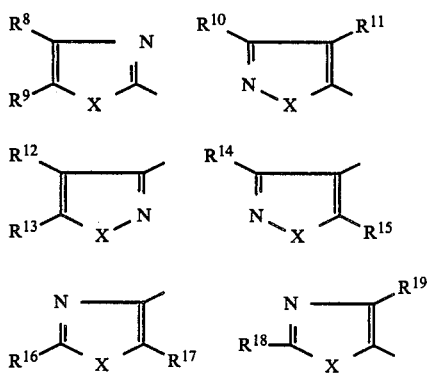

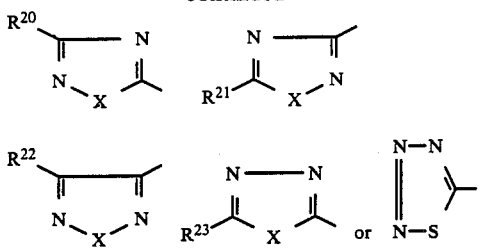

wherein

X in each case represents oxygen or sulphur and
$R^8$ to $R^{23}$, which can be identical or different, individually represent hydrogen, bromine, chlorine, nitro, amino, cyano, $C_1$–$C_3$-alkyl-carbonyl, $C_1$–$C_3$-alkoxycarbonyl, phenyl (which is optionally monosubstituted or disubstituted, the substituent(s) being selected from fluorine, chlorine, bromine, methyl, halogenomethyl, methoxy, nitro and cyano), phenoxy or phenylthio, $C_1$–$C_4$-alkylthio or $C_1$–$C_4$-alkoxy, $C_1$–$C_4$-alkylsulphinyl or $C_1$–$C_4$-alkylsulphonyl, $C_1$–$C_4$-alkyl, trifluoromethyl, trichloromethyl, cyano-$C_1$–$C_4$-alkyl, $C_2$–$C_4$-alkenyl, benzyloxymethyl, $C_1$–$C_3$-alkyl-amino, N-$C_1$–$C_3$-alkyl-N-$C_1$–$C_4$-alkyl-aminocarbonyl, benzylthio, phenoxymethyl.

If, for example, 2,4,5-trichloro-1,3-thiazole and hydroxyacetic acid piperidide are used as starting materials, the course of the reaction in the process according to the invention can be represented by the following equation:

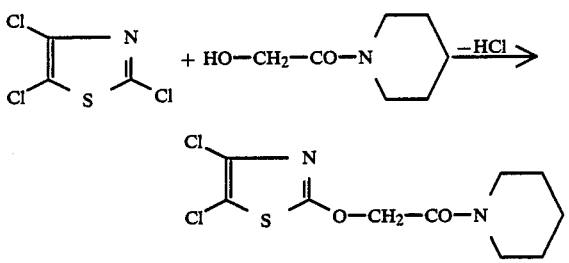

Formula (II) provides a definition of the α-hydroxycarboxylic acid amides to be used as starting materials. In this formula, $R^1$, $R^2$ and $R^3$ preferably have those meanings which have already been mentioned as preferred or particularly preferred in connection with the definitions of the compounds of the formula (I) or (Ia).

Examples of starting compounds of the formula (II) which may be mentioned are: hydroxyacetic acid dimethylamide, diethylamide, di-n-propyl-amide, di-iso-propyl-amide, N-methyl-N-iso-propyl-amide, N-methyl-N-n-butyl-amide, N-methyl-N-iso-butyl-amide, N-methyl-N-sec.-butyl-amide, N-ethyl-N-iso-propyl-amide, N-ethyl-N-n-butylamide, N-propyl-N-sec.-butyl-amide, N-methyl-N-(2-cyano-ethyl)-amide, di-(2-methoxyethyl)-amide, di-allyl-amide, N-methyl-N-propargyl-amide, N-methyl-N-(1-methyl-propargyl)-amide, dipropargyl-amide, cyclopentyl-amide, N-methyl-N-cyclopentyl-amide, cyclohexyl-amide, N-methyl-N-cyclohexyl-amide, N-ethyl-N-cyclohexylamide, anilide, 2-nitro-, 3-nitro- and 4-nitro-phenyl-amide, 2-chloro-, 3-chloro- and 4-chloro-phenyl-amide, 2,4-dichloro, 2,5-dichloro-, 3,4-dichloro- and 3,5-dichloro-phenyl-amide, 2-methyl-, 3-methyl- and 4-methyl-phenyl-amide, N-allyl-anilide, N-propargyl-anilide, N-methyl-anilide, N-ethyl-anilide, N-methyl-N-(2-nitro-phenyl)-N-methyl-N-(3-nitro-phenyl)- and N-methyl-N-(4-nitro-phenyl)-amide, N-methyl-N-(2-chloro-phenyl)-, N-methyl-N-(3-chloro-phenyl)- and N-methyl-N-(4-chloro-phenyl)-amide, N-methyl-N-(3-nitro-6-methyl-phenyl)-amide, N-methyl-N-(2-methyl-phenyl)-amide, N-ethyl-anilide, N-ethyl-N-(2-nitro-phenyl)-, N-ethyl-N-(3-nitro-phenyl)- and N-ethyl-N-(4-nitro-phenyl)-amide, N-ethyl-N-(2-chloro-phenyl)-, N-ethyl-N-(3-chloro-phenyl)- and N-ethyl-N-(4-chloro-phenyl)-amide, N-ethyl-N-(3-nitro-6-methyl-phenyl)-amide, N-propyl-anilide, N-propyl-N-(2-nitro-phenyl)-, N-propyl-N-(3-nitro-phenyl)- and N-propyl-N-(4-nitro-phenyl)-amide, N-propyl-N-(2-chloro-phenyl)-, N-propyl-N-(3-chloro-phenyl)- and N-propyl-N-(4-chloro-phenyl)-amide, N-propyl-N-(2-methyl-phenyl)-, N-propyl-N-(3-methyl-phenyl)- and N-propyl-N-(4-methyl-phenyl)-amide, N-propyl-N-(3-nitro-6-methyl-phenyl)-amide, N-butyl-anilide, N-butyl-N-(2-nitro-phenyl)-N-butyl-N-(3-nitro-phenyl)- and N-butyl-N-(4-nitro-phenyl)-amide, N-butyl-N-(2-chloro-phenyl)-, N-butyl-N-(3-chloro-phenyl)- and N-butyl-N-(4-chloro-phenyl)-amide, N-butyl-N-(2-methyl-phenyl)-, N-butyl-N-(3-methyl-phenyl)- and N-butyl-N-(4-methyl-phenyl)-amide, N-butyl-N-(3-nitro-6-methyl-phenyl)-amide, N-isobutyl-anilide, N-iso-butyl-N-(2-nitro-phenyl)-, N-iso-butyl-N-(3-nitro-phenyl)- and N-iso-butyl-N-(4-nitro-phenyl)-amide, N-iso-butyl-N-(2-chloro-phenyl)-, N-iso-butyl-N-(3-chloro-phenyl)- and N-iso-butyl-N-(4-chlorophenyl)-amide, N-iso-butyl-N-(2-methyl-phenyl)-, N-iso-butyl-N-(3-methyl-phenyl)- and N-iso-butyl-N-(4-methylphenyl)-amide, N-iso-butyl-N-(3-nitro-6-methyl-phenyl)amide, naphth-1-ylamide, naphth-2-ylamide, N-methyl-N-naphth-1-ylamide, N-methyl-N-naphth-2-ylamide, N-ethyl-N-naphth-1-ylamide, N-ethyl-N-naphth-2-ylamide, N-n-propyl-N-naphth-2-ylamide, N-iso-propyl-N-naphth-2-ylamide, N-n-butyl-N-naphth-2-ylamide, N-iso-butyl-N-naphth-2-ylamide, benzylamide, dibenzylamide, N-methyl-N-benzylamide, N-ethyl-N-benzylamide, N-propyl-N-benzylamide, N-butyl-N-benzylamide, N-allyl-N-benzyl-amide, N-propargyl-N-benzylamide, pyrrolidide, 2-methyl-pyrrolidide, morpholide, piperidide, 2-methyl-piperidide, 4-methyl-piperidide, 3,5-dimethyl-piperidide, 2,4-dimethyl-piperidide, 2,3,4-trimethyl-piperidide, 2,4,6-trimethyl-piperidide, 2-ethyl-piperidide, 4-ethyl-piperidide, 2,4-diethyl-piperidide, 2,3,4-triethyl-piperidide, 2,4,6-triethyl-piperidide, 2-methyl-4-ethyl-piperidide, 2-ethyl-4-methyl-piperidide, 2-methyl-5-ethyl-piperidide, 2-ethyl-5-methyl-piperidide, 2-methyl-6-ethyl-piperidide, 1,2,3,4-tetrahydroindolide, 2-methyl-1,2,3,4-tetrahydroindolide, perhydroindolide, 2-methyl-perhydroindolide, 2,2-dimethyl-perhydroindolide, 1,2,3,4-tetrahydroquinolide, 2-methyl-1,2,3,4-tetrahydroquinolide, 4-methyl-1,2,3,4-tetrahydroquinolide, perhydroquinolide, 2-methyl-perhydroquinolide, 1,2,3,4-tetrahydro-isoquinolide, perhydroisoquinolide and perhydroazepinide.

Some of the α-hydroxy-carboxylic acid amides of the formula (II) are shown (see U.S. Pat. No. 3,399,988 and DE-OS (German Published Specifications Nos. 2,201,432 and 2,647,481). The compounds (II) can be prepared from α-chloro-carboxylic acid chlorides, as outlined in the equation below:

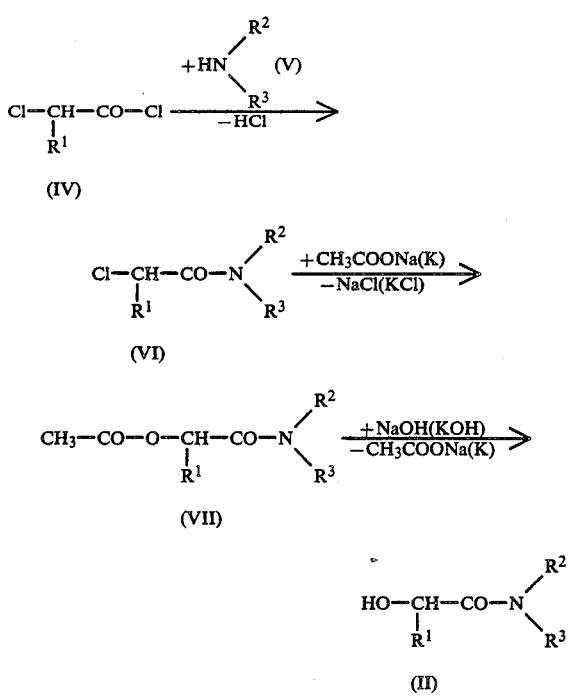

In this preparation, the α-chloro-carboxylic acid chlorides of the formula (IV), which are known from the literature, are first converted into the corresponding chlorocarboxylic acid amides of the formula (VI) with amines of the formula (V), $R^1$, $R^2$ and $R^3$ having the meanings indicated above, if appropriate in the presence of an acid-binding agent, for example triethylamine, and if appropriate using an inert diluent, for example 1,2-dichloroethane, at temperatures between −20° and 100° C., preferably between −10° and 50° C. These products are worked up by customary methods, by washing with water, drying the organic phase and distilling off the solvent.

The compounds of the formula (VI) are reacted with sodium acetate or potassium acetate, if appropriate using a diluent, for example acetic acid or dimethylsulphoxide, at temperatures between 20° and 150° C., preferably between 50° and 120° C., to give the corresponding α-acetoxy-carboxylic acid amides of the formula (VII). If the products are obtained as crystals in this reaction, they are isolated by filtration. Otherwise, working up is effected by customary methods, for example by distilling off the solvent in vacuo, taking up the residue in methylene chloride, washing the methylene chloride mixture with water and distilling off the solvent.

The compounds of the formula (VII) can be deacylated to give the compounds of the formula (II) by reaction with aqueous-alcoholic sodium hydroxide solution or potassium hydroxide solution at temperatures between 0° and 100° C., preferably between 10° and 50° C. To isolate the products, the solvents are distilled off in vacuo, the residue is extracted with an organic solvent, for example methylene chloride or ethyl acetate, the solution is dried and the solvent is distilled off.

Formula (III) provides a definition of the halogenoazoles also to be used as starting materials. In this formula, R preferably has those meanings which have already been mentioned as preferred or particularly preferred in connection with the definitions of the compounds of the formula (I) or (Ia), and Hal preferably represents chlorine or bromine.

Examples of starting substances of the formula (III) which may be mentioned are: 2-chloro- and 2-bromo-oxazole and -thiazole, 2,4-dichloro-, 2,5-dichloro- and 2,4,5-trichloro-oxazole and -thiazole, 4-methyl-, 5-methyl-, 4-tert.-butyl-, 4,5-dimethyl-, 4-methyl-5-chloro-, 5-methyl-4-chloro, 4-methyl-5-methoxycarbonyl-, 4-methyl-5-ethoxycarbonyl-, 4-methyl-5-isopropoxycarbonyl-, 4-methyl-5-acetyl-, 5-phenyl-, 4,5-diphenyl-, 4-chloro-5-phenyl-, 4-chloro-5-(3,4-dichloro-phenyl)- and 4-methyl-5-phenylthio-2-chloro-oxazole, -2-bromo-oxazole, -2-chloro-thiazole and -2-bromo-thiazole; 4-methyl-5-cyano-2-chloro- and 4-phenyl-5-cyano-2-chloro-thiazol; 3-tert.-butyl-4-cyano-, 3-but-3-en-1-yl-, 3,4-bis-ethoxycarbonyl-, 3-phenyl-, 3-ethyl-4-phenyl-5-chloro-isoxazole, -5-chloro-isothiazole, -5-bromo-isoxazole and -5-bromo-isothiazole; 3,5-bis-ethoxycarbonyl-4-chloro- and 3,5-bis-ethoxycarbonyl-4-bromo-isoxazole and -isothiazole; 3,5-dichloro-1,2,4-oxadiazole, 3-methyl-, 3-ethyl-, 3-n-propyl-, 3-isopropyl-, 3-tert.-butyl-, 3-trifluoromethyl-, 3-trichloromethyl-, 3-phenyl-, 3-(4-trifluormethyl-phenyl)-, 3-(3-trifluormethyl-phenyl)-, 3-methylthio-, 3-methylsulphinyl-, 3-methylsulphonyl-5-chloro-1,2,4-thiadiazole and -5-bromo-1,2,4-thiadiazole; 4-methyl-, 4-ethyl-, 4-n-propyl- and 4-iso-propyl-3-chloro-1,2,5-thiadiazole and -3-bromo-1,2,5-thiadiazole; 2-chloro- and 2-bromo-1,3,4-oxadiazole, 2-chloro- and 2-bromo-1,3,4-thiadiazole and 5-methyl-, 5-ethyl-, 5-n-propyl-, 5-iso-propyl-, 5-tert.-butyl-, 5-phenyl-, 5-(4-trifluormethyl-phenyl)-, 5-(3-trifluormethyl-phenyl)-, 5-bromo-, 5-methylsulphinyl-, 5-ethylsulphinyl-, 5-propylsulphinyl-, 5-methylsulphonyl-, 5-ethylsulphonyl-, 5-propyl-sulphonyl-, 5-methoxycarbonyl-, 5-ethoxy-carbonyl-, 5-(1-cyano-2-methyl-propyl)-, 5-benzyloxymethyl-, 5-acetylamino-, 5-nitro-, 5-propylthio-, 5-trifluoromethyl-, 5-trichloromethyl-, 5-methylamino- and 5-(N-methyl-N-tert.-butylcarbonyl-amino)-2-chloro-1,3,4-oxadiazole, -2-bromo-1,3,4-oxadiazole, -2-chloro-1,3,4-thiadiazole and -2-bromo-1,3,4-thiadiazole.

Halogenoazoles of the formula (III) are in general known (see Elderfield, Heterocyclic Compounds, Volume 5 (1957), page 298 and page 452; Volume 7 (1961), page 463 and page 541; Weissberger, The Chemistry of Heterocyclic Compounds, (a) "Five-Membered Heterocyclic Compounds with Nitrogen and Sulphur or Nitrogen, Sulphur and Oxygen" (1952), page 35 and page 81 and (b) "Five- and Six-Membered Compounds with Nitrogen and Oxygen" (1962), page 5, page 245 and page 263; Advances in Heterocyclic Chemistry, Volume 5 (1965), page 119; Volume 7 (1966), page 183; Volume 9 (1968), page 107, page 165 and page 183; Volume 17 (1974), page 99 and Volume 20 (1976), page 65; Synthesis 1978, 803; Tetrahedron Letters 1968, 829; Chem. Ber. 89 (1956), 1534; 90 (1957), 182; and 92 (1959) 1928; J. Org. Chem. 27 (1962), 2589 and DE-OS (German Published Specification No.) 2,213,865).

Some of the halogenoazoles to be used as starting substances have not yet been described in the literature. Various halogeno-azoles are obtained, for example, by dissolving corresponding amino-azoles in water, with hydrogen halide acids, and reacting them with sodium nitrite, whilst cooling with ice, stirring the mixture at temperatures between 10° and 50° C. for some hours, extracting the products with toluene and, after washing and drying, working up the organic phase by distillation (see DE-OS (German Published Specification No.) 2,144,326).

The process, according to the invention, for the preparation of the azolyloxycarboxylic acid amides (I) is preferably carried out using a suitable solvent or diluent. Possible solvents or diluents are virtually any of the inert organic solvents. These include, as preferences, alcohols, such as methanol, ethanol, n- and iso-propanol and n-, iso-, sec.- and tert.-butanol; ethers, such as diethyl ether, dibutyl ether, tetrahydrofuran and dioxan; ketones, such as acetone, methyl ethyl ketone, methyl isopropyl ketone and methyl isobutyl ketone; nitriles, such as acetonitrile and propionic acid nitrile; and the highly polar solvents dimethylformamide, dimethylsulphoxide, sulpholane and hexamethylphosphoric acid triamide.

Virtually any of the acid-binding agents which can customarily be used can be employed as an acid acceptor in the process according to the invention. Preferred acid acceptors include alkali metal hydroxides and oxides and alkaline earth metal hydroxides and oxides, such as sodium hydroxide and potassium hydroxide and calcium oxide or calcium hydroxide; alkali metal carbonates and alkaline earth metal carbonates, such as sodium carbonate, potassium carbonate and calcium carbonate; alkali metal alcoholates, such as sodium methylate, ethylate and tert.-butylate and potassium methylate, ethylate and tert.-butylate; and aliphatic, aromatic or heterocyclic amines, such as triethylamine, dimethylaniline, dimethylbenzylamine, pyridine, diazabicyclooctane and diazabicycloundecene.

The reaction temperatures can be varied within a substantial range. In general, the reaction is carried out at from $-50°$ to $+150°$ C., preferably at from $-20°$ to $+100°$ C.

The process according to the invention is in general carried out under normal pressure.

In carrying out the process according to the invention, 1.0 to 1.5 moles of α-hydroxy-carboxylic acid amide of the formula (II) are in general employed per mole of halogenoazole of the formula (III). The reaction is in general carried out in a suitable diluent and the reaction mixture is stirred at the required temperature for several hours.

The products are isolated by customary methods: if appropriate, part of the diluent is distilled off under reduced pressure and the remainder of the reaction mixture is poured into water. If the products are obtained as crystals in this procedure, they are isolated by filtration. Otherwise, the organic products are extracted with a water-immiscible solvent, for example toluene or methylene chloride; after washing and drying, the solvent is then distilled off from the organic phase in vacuo. The products which remain are characterised by their melting point or their refractive index.

The active compounds according to the invention influence plant growth and can therefore be used as defoliants, desiccants, agents for destroying plants, germination inhibitors and, especially, as weed-killers. By "weeds" in the broadest sense there are meant plants growing in places where they are not desired.

Whether the compounds according to the invention act as total herbicides or selective herbicides depends essentially on the amount used.

The active compounds according to the present invention may be used, for example, to combat the following plants:

dicotyledon weeds of the genera Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Rorippa, Rotala, Lindernia, Lamium, Veronica, Abutilon, Emex, Datura, Viola, Galeopsis, Papaver, Centaurea and Solanum; and monocotyledon weeds of the genera Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

The active compounds according to the present invention may be used, for example, as selective herbicides in the following cultures:

dicotyledon cultures of the genera Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Curcurbita; and monocotyledon cultures of the genera Oryza, Zea, Triticum, Hordeum, Avena, Secale, Sorghum, Panicum, Saccharum, Ananas, Asparagus and Allium.

However, the use of the active compounds according to the invention is in no way restricted to these genera but also embraces other plants, in the same way.

Depending on the concentrations, the compounds can be used for the total combating of weeds, for example on industrial terrain and railway tracks and on paths and squares with or without trees. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cacao plantations, soft fruit plantings and hopfields, and for the selective combating of weeds in annual cultures.

In particular, the active compounds according to the invention also exhibit a good herbicidal action against broad-leafed weeds, in addition to a very good action against graminaceous weeds. It is possible to use the active compounds according to the invention selectively in various crops, for example in beet, soya bean, cotton, rice and other varieties of cereal. Individual active compounds are particularly suitable as selective herbicides in beet, cotton and cerals.

The active compounds can be converted to the customary formulations, such as solutions, emulsions, wettable powders, suspensions, powders, dusting agents, pastes, soluble powders, granules, suspension-emulsion concentrates, natural and synthetic materials impregnated with active compound, and very fine capsules in polymeric substances.

These formulations may be produced in known manner, for example by mixing the active compounds with extenders, that is to say liquid or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention, as such or in the form of their formulations, can also be used, for combating weeds, as mixtures with other herbicides, finished formulations or tank mixing being possible. Mixtures with other active compounds, such as fungicides, insecticides, acaricides, nematicides, bird repellants, growth factors, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They may be used in the customary manner, for example by watering, spraying, atomizing, scattering or dusting.

The active compounds according to the invention can be applied either before or after emergence of the plants. They are preferably applied before emergence of the plants, that is to say by the pre-emergence method. They can also be incorporated into the soil before sowing.

The amount of active compound used can vary within a substantial range. It depends essentially on the nature of the desired effect. In general, the amounts used are from 0.01 to 10 kg of active compound per ha, preferably from 0.1 to 5 kg/ha.

When applied in certain concentrations, some of the active compounds according to invention also display a growth regulating action.

The present invention also provides a herbicidal composition containing as active ingredient a compound of the present invention in admixture with a solid diluent or carrier or in admixture with a liquid diluent or carrier containing a surface-active agent.

The present invention also provides a method of combating weeds which comprises applying to the weeds, or to a habitat thereof, a compound of the present invention alone or in the form of a composition containing as active ingredient a compound of the present invention in admixture with a diluent or carrier.

The present invention further provides crops protected from damage by weeds by being grown in areas in which immediatetly prior to and/or during the time of the growing a compound of the present invention was applied alone or in admixture with a diluent or carrier.

It will be seen that the usual methods of providing a harvested crop may be improved by the present invention.

The herbicidal activity of the compounds of this invention is illustrated by the following biotest Example.

In this Example, the compounds according to the present invention are each identified by the number (given in brackets) of the corresponding preparative Example, which will be found later in this specification.

EXAMPLE A

Pre-emergence Test

Solvent: 5 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

Seeds of the test plants were sown in normal soil and, after 24 hours, watered with the preparation of the active compound. It was expedient to keep constant the amount of water per unit area. The concentration of the active compound in the preparation was of no importance, only the amount of active compound applied per unit area being decisive. After three weeks, the degree of damage to the plants was determined in % damage in comparison to the development of the untreated control. The figures denoted:

0%=no action (like untreated control)
100%=total destruction

In this test, for example, the following compounds exhibited an excellent action: (1), (2), (8), (17), (19), (31), (41), (99), (104), (107), (108), (118), (119), (120), (121), (122), (123), (124), (125), (126), (129), (130), (131), (132), (141), (142), (145), (154), (155), (156), (159), (160), (162), (163), (168), (180), (184), (187), (188), (189), (190), (193), (194), (195), (196), (248),

EXAMPLE B

Pre-emergence water-surface treatment under flooded conditions for paddy field weeds (Pot test)

Preparation of Active Compounds

Solvent: 5 parts by weight of acetone

Emulsifier: 1 part by weight of benzyloxy-polyglycol ether

To produce a suitable preparation of active compound, 1 part by weight of active compound was mixed with the stated amount of solvent, the stated amount of emulsifier was added and the concentrate was diluted with water to the desired concentration.

Test Method

Pots (1/5,000 are) were filled with paddy field soil. Two rice plants (variety: Kinmaze) per pot at the 2- or 3-leaves stage (about 10 cm high) were transplanted. Echinochloa crus-galli, Cyperus sp., broadleaf weed seeds and Eleocharis acicularis L. were inoculated and maintained in wet condition. Two days after transplantation, each pot was placed in flooded condition to a depth of 3 cm. Then the active compound was applied by watering with the preparation of the active compound. After treatment, water in pots was being leached for two days at a rate of 2 to 3 cm per day. After this leaching, each pot was maintained in flooded condition to a depth of 3 cm. Four weeks after treatment with chemicals, herbicidal efficacy and phytotoxicity against rice plants were determined on a scale of the six grades (0 to 5) shown below in comparison to the untreated plant.

| efficacy | phytotoxicity |
|---|---|
| 5 More than 95% | 5 More than 90% (completely injured) |
| 4 more than 80% | 4 more than 50% |
| 3 more than 50% | 3 more than 30% |
| 2 more than 30% | 2 less than 30% |
| 1 more than 10% | 1 less than 10% |
| 0 less than 10% | 0 0% (no phytotoxicity) |

In this test, for example, the following compounds exhibited an excellent action:

(1), (6), (7), (8), (9), (10), (13), (16), (17), (19), (20), (21), (24), (26), (29), (32), (41), (51), (52), (54), (55), (56), (77), (78), (97), (99), (104), (106), (108), (111), (130), (131), (132), (134), (135), (138), (141), (142), (146), (149), (153), (154), (155), (156), (248)

PREPARATIVE EXAMPLES

Example 1

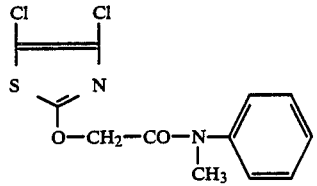 (1)

14.8 g (0.09 mol) of hydroxyacetic acid N-methylanilide were dissolved in 100 ml of isopropanol. The solution was stirred with 5.6 g of powdered potassium hydroxide and the mixture was cooled to −15° C. 13.1 g (0.07 mol) of 2,4,5-trichlorothiazole were added dropwise at −15° C. in the course of one hour. The mixture was stirred at −10° C. for 3 hours, the temperature was then allowed to rise to 0° C. and the mixture was stirred at 0° C. for 2 hours and then at room temperature for 10 hours. ¾ of the solvent were then distilled off, the residue was poured onto water and the solid which precipitated was filtered off and dried. The yield was 18 g (81% of theory) of O-(4,5-dichloro-1,3-thiazol-2-yl)-oxyacetic acid N-methylanilide; melting point: 82° C.

Example 2

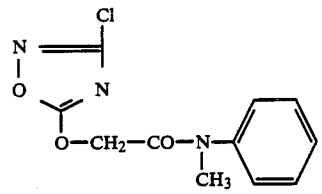 (2)

9 g (0.05 mol) of hydroxyacetic acid N-methylanilide were dissolved in 100 ml of acetonitrile. 7.6 g of potassium carbonate were then added. 6.9 g of 3,5-dichloro-1,2,4-oxadiazole were slowly added dropwise at −10° C. The mixture was then subsequently stirred at −10° C. for a further 2 hours, at 0°–5° C. for 3 hours and at room temperature for 20 hours. The acetonitrile was then distilled off in vacuo until ¼ remained, the residue was poured onto water and the product was extracted with toluene. After distilling off the toluene, the substance crystallised. The yield was 9 g (70% of theory) of O-(3-chloro-1,2,4-oxadiazol-5-yl)-oxyacetic acid N-methylanilide; melting point: 73° C.

Example 3

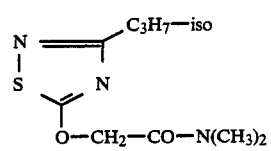 (3)

8.6 g (0.082 mol) of hydroxyacetic acid dimethylamide were stirred in 150 ml of tert.-butanol together with 11.2 g of potassium tert.-butylate. 13.3 g of 5-chloro-3-isopropyl-1,2,4-thiadiazole were slowly added dropwise at 20° C. The mixture was stirred at about 40° C. for 4 hours. ¾ of the tert.-butanol was then distilled off in vacuo and the residue was poured onto water. The oil which precipitated was extracted with toluene. After distilling off the toluene, the product—O-(3-isopropyl-1,2,4-thiadiazol-5-yl)-oxyacetic acid dimethylamide—remained as crystals, in a yield of 9 g (50% of theory) and with a boiling point of 67° C.

Example 4

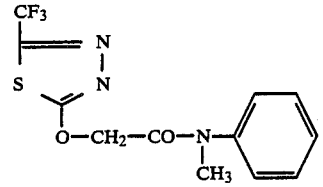 (4)

8.7 g (0.05 mol) of 2-hydroxyacetic acid N-methylanilide were stirred in 60 ml of dimethylsulphoxide together with 3 g of calcium oxide at 50° C. for 1 hour. 11.6 g of 5-bromo-2-trifluoromethyl-1,3,4-thiadiazole were then added dropwise at 50° C. and the mixture was subsequently stirred at 50° C. for 40 hours. The solution was then poured onto 1 liter of water and the oil which had precipitated was extracted with methylene chloride. After distilling off the methylene chloride, the product—O-(2-trifluoromethyl-1,3,4-thiadiazol-5-yl)-oxyacetic acid N-methylanilide—remained as an oil, in a yield of 10 g and with a refractive index of $n_D^{21}$: 1.5404.

Example 5

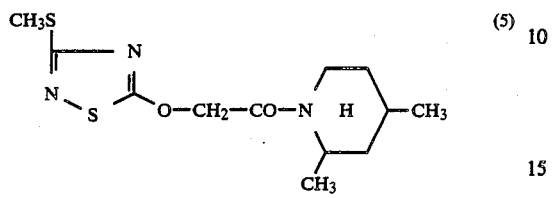

8.3 g (0.05 mol) of 5-chloro-3-methylthio-1,2,4-thiadiazole were added to a mixture of 8.5 g (0.05 mol) of hydroxyacetic acid 2,4-dimethylpiperidide, 3.4 g (0.06 mol) of potassium hydroxide powder, 1 g of copper powder and 100 ml of isopropanol at 20°–30° C. The mixture was stirred for several hours and then diluted with water, the product was then extracted with toluene, the organic phase was washed with water, dried and filtered and the solvent was stripped off from the filtrate in vacuo. The yield was 9 g (60% of theory) of O-(3-methylthio-1,2,4-thiadiazol-5-yl)-oxyacetic acid N-(2,4-dimethylpiperidide); refractive index: $n_D^{23}$: 1.5460.

The following compounds of the general formula

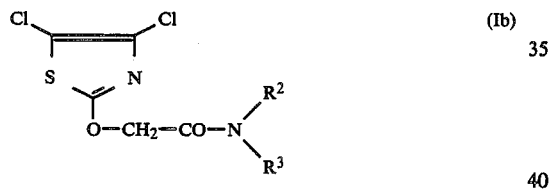

could be prepared analogously to one of Examples 1 to 5:

TABLE 1

| Example No. | $-N\begin{matrix}R^2\\R^3\end{matrix}$ | Physical data (Refractive index; melting point °C.) |
|---|---|---|
| 6 | 2-methylpiperidinyl | $n_D^{23}$: 1.5449 |
| 7 | 4-methylpiperidinyl | 38 |
| 8 | —N(CH₃)₂ | 85 |
| 9 | —N(C₂H₅)₂ | $n_D^{23}$: 1.5399 |
| 10 | —N(CH₂—CH=CH₂)₂ | $n_D^{23}$: 1.5418 |
| 11 | —N(cyclohexyl)₂ | 127 |
| 12 | morpholino | 125 |
| 13 | hexamethyleneimino | 62 |
| 14 | pyrrolidino | 63 |
| 15 | —N(C₃H₇—iso)₂ | 68 |
| 16 | N-methyl-N-cyclohexyl | $n_D^{21}$: 1.5510 |
| 17 | —N(CH(CH₃))—C≡CH (with H₃C, CH₃) | |
| 18 | —N(CH₂—CH₂—OCH₃)₂ | |
| 19 | —N—CH(CH₃)—CH₂—CH₃ (with CH₃) | $n_D^{25}$: 1.5357 |
| 20 | N-methyl-N-(2-methylphenyl) | 88–90 |
| 21 | 2-ethylpiperidinyl | $n_D^{21}$: 1.5440 |
| 22 | 3,3,5-trimethyl ring (CH₃, CH₃, CH₃) | 99 |
| 23 | 3,3,5-trimethylhexamethyleneimino | 90 |

TABLE 1-continued

| Example No. | −N(R²)(R³) | Physical data (Refractive index; melting point °C.) |
|---|---|---|
| 24 | N-morpholinyl with 2,6-dimethyl (−N<(CH(CH₃)−O−CH(CH₃)−CH₂−)) | $n_D^{21}$: 1.5549 |
| 25 | −N(C₂H₅)(cyclohexyl) | 103 |
| 26 | 1,2,3,4-tetrahydroquinolin-1-yl | $n_D^{22}$: 1.6083 |
| 27 | decahydroquinolin-1-yl | $n_D^{22}$: 1.5570 |
| 28 | −N(CH₂C₆H₅)(C₆H₅) | $n_D^{22}$: 1.5972 |
| 29 | 2,4-dimethylpiperidin-1-yl | $n_D^{22}$: 1.5432 |
| 30 | 4-ethylpiperidin-1-yl | $n_D^{22}$: 1.5500 |

The following compounds could be prepared analogously:

| Example No. | Formula | Physical data (Refractive index; Melting point °C.) |
|---|---|---|
| 31 | CH₃S−C(=N−S−N=)−C(=O)−O−CH₂−CO−N(2-methylpiperidin-1-yl) | $n_D^{23}$: 1.5560 |
| 32 | CH₃S−C(=N−S−N=)−C(=O)−O−CH₂−CO−N(CH₃)(C₆H₅) | 98 |
| 33 | CH₃S−C(=N−S−N=)−C(=O)−O−CH₂−CO−N(C₂H₅)₂ | 68 |
| 34 | CH₃S−C(=N−S−N=)−C(=O)−O−CH₂−CO−N(CH₃)₂ | 150 |
| 35 | CH₃S−C(=N−S−N=)−C(=O)−O−CH₂−CO−N(hexamethyleneimino) | $n_D^{23}$: 1.5440 |

-continued

| Example No. | Formula | Physical data (Refractive index; Melting point °C.) |
|---|---|---|
| 36 | CH₃S-C(=N-N=S-)-O-CH₂-CO-N(morpholine) | 156 |
| 37 | Cl₂C=C(-S-N=)-C(CH₃)H-O-CO-N(CH₃)(C₆H₅) | $n_D^{22}$: 1.5584 |
| 38 | n-C₃H₇-SO₂-C(=N-N=S-)-O-CH₂-CO-N(CH₃)(C₆H₅) | $n_D^{23}$: 1.5675 |
| 39 | CH₃-SO₂-C(=N-N=S-)-O-CH₂-CO-N(CH₃)(C₆H₅) | $n_D^{23}$: 1.5534 |
| 40 | C₂H₅-SO₂-C(=N-N=S-)-O-CH₂-CO-N(CH₃)(C₆H₅) | $n_D^{23}$: 1.5321 |
| 41 | CH₃-C(=)(N-S-N=)-O-CH₂-CO-N(CH₃)(C₆H₅) | 64 |
| 42 | iso-C₃H₇-C(=)(N-S-N=)-O-CH₂-CO-N(CH₃)(C₆H₅) | 120 |
| 43 | iso-C₃H₇-C(=)(N-S-N=)-O-CH₂-CO-N(3-methylpiperidine) | $n_D^{23}$: 1.5135 |
| 44 | iso-C₃H₇-C(=)(N-S-N=)-O-CH₂-CO-N(C₂H₅)₂ | 44 |
| 45 | iso-C₃H₇-C(=)(N-S-N=)-O-CH₂-CO-N(CH₂-CH=CH₂)₂ | $n_D^{23}$: 1.5142 |

-continued

| Example No. | Formula | Physical data (Refractive index; Melting point °C.) |
|---|---|---|
| 46 | iso-C₃H₇ group with thiadiazole (N—S, N), —O—CH₂—CO—N(morpholine) | 72 |
| 47 | iso-C₃H₇ group with thiadiazole, —O—CH₂—CO—N(pyrrolidine) | 54 |
| 48 | 3,4-dichlorophenyl, Cl, thiazole ring, —O—CH₂—CO—N(CH₃)(phenyl) | 118 |
| 49 | iso-C₃H₇ group with thiadiazole, —O—CH₂—CO—N(4-methylpiperidine) | 56 |
| 50 | iso-C₃H₇ group with thiadiazole, —O—CH₂—CO—N(CH₃)—CH₂—C≡CH | $n_D^{21}$: 1.5230 |
| 51 | iso-C₃H₇ group with thiadiazole, —O—CH₂—CO—N(CH₃)—CH(CH₃)—C≡CH | $n_D^{21}$: 1.5155 |
| 52 | iso-C₃H₇ group with thiadiazole, —O—CH₂—CO—N(2,6-dimethylmorpholine) | $n_D^{21}$: 1.5140 |
| 53 | iso-C₃H₇ group with thiadiazole, —O—CH₂—CO—N(CH₂—CH₂—OCH₃)₂ | $n_D^{21}$: 1.4987 |
| 54 | iso-C₃H₇ group with thiadiazole, —O—CH₂—CO—N(CH₃)(cyclohexyl) | $n_D^{21}$: 1.5150 |

-continued

| Example No. | Formula | Physical data (Refractive index; Melting point °C.) |
|---|---|---|
| 55 | iso-C$_3$H$_7$-C(=N-S-N=)-O-CH$_2$-CO-N(CH$_3$)-CH(CH$_3$)-CH$_2$-CH$_3$ | 46–48 |
| 56 | iso-C$_3$H$_7$-C(=N-S-N=)-O-CH$_2$-CO-N(CH$_3$)-(o-CH$_3$-C$_6$H$_4$) | $n_D^{21}$: 1.5428 |
| 57 | (CH$_3$)$_3$C-C(=N-N=)(S)-O-CH$_2$-CO-N(CH$_3$)-C$_6$H$_5$ | 85–86 |
| 58 | (CH$_3$)$_3$C-C(=N-N=)(S)-O-CH$_2$-CO-N(H)(2-CH$_3$-piperidine) | 84–85 |
| 59 | C$_6$H$_5$-C(=C(Cl)-)-C(=N-S-)-O-CH$_2$-CO-N(H)(2-CH$_3$-piperidine) | $n_D^{20}$: 1.5881 |
| 60 | iso-C$_3$H$_7$-C(=N-S-N=)-O-CH$_2$-CO-N(CH$_2$CH$_2$CH$_3$)-CH(CH$_3$)-CH$_2$-CH$_3$ | $n_D^{20}$: 1.4949 |
| 61 | (CH$_3$)$_3$C-C(=N-N=)(S)-O-CH$_2$-CO-N(CH$_3$)$_2$ | 78 |
| 62 | 4,5-diphenyl-oxazol-2-yl-O-CH$_2$-CO-N(CH$_3$)-C$_6$H$_5$ | 103 |

| Example No. | Formula | Physical data (Refractive index; Melting point °C.) |
|---|---|---|
| 63 | (diphenyl oxazole)-O-CH$_2$-CO-N(H)(2-ethylpiperidine) | 116 |
| 64 | (diphenyl oxazole)-O-CH$_2$-CO-N(CH$_3$)-CH(CH$_3$)-CH$_2$-CH$_3$ | 134 |
| 65 | (diphenyl oxazole)-O-CH$_2$-CO-N(H)(2-methylpiperidine) | 156 |
| 66 | (diphenyl oxazole)-O-CH$_2$-CO-N(morpholine) | 110 |
| 67 | (diphenyl oxazole)-O-CH$_2$-CO-N(CH$_2$-CH$_2$-OCH$_3$)$_2$ | 92 |

-continued

| Example No. | Formula | Physical data (Refractive index; Melting point °C.) |
|---|---|---|
| 68 | 4,5-diphenyloxazol-2-yl-O-CH₂-CO-N(azepane) | 143 |
| 69 | 4,5-diphenyloxazol-2-yl-O-CH₂-CO-N(2,6-dimethylmorpholine) | 93 |
| 70 | 4,5-diphenyloxazol-2-yl-O-CH₂-CO-NH(piperidine) | 143 |
| 71 | 4,5-diphenyloxazol-2-yl-O-CH₂-CO-N(3,3-dimethylpiperidine with CH₂) | 133 |
| 72 | 4,5-diphenyloxazol-2-yl-O-CH₂-CO-N(2,2,5-trimethylazepane) | 90 |
| 73 | 3-phenylisoxazol-5-yl-O-CH₂-CO-N(CH₃)(phenyl) | 138 |

-continued

| Example No. | Formula | Physical data (Refractive index; Melting point °C.) |
|---|---|---|
| 74 | (structure: 3-ethyl-4-phenyl-isoxazol-5-yl-O-CH₂-CO-N(CH₃)-phenyl) | |
| 75 | (structure: 5-phenyl-isoxazol-3-yl-O-CH₂-CO-N(CH₃)-phenyl) | 110 |
| 76 | (structure: 3-(C₂H₅OCO)-4-(O-CH₂-CO-N(CH₃)-phenyl)-5-(CO-OC₂H₅)-isoxazole) | $n_D^{21}$: 1.5334 |
| 77 | (structure: (CH₃)₂CH-O-, CH₃ substituted thiazoline with O-CH₂-CO-N(CH₃)-phenyl) | 115 |
| 78 | (structure: 2-phenyl-1,3,4-thiadiazol-5-yl-O-CH₂-CO-N(CH₃)-phenyl) | 114 |
| 79 | (structure: 4-phenyl-thiazol-2-yl-O-CH₂-CO-N(CH₃)-phenyl) | 107 |
| 80 | (structure: 4-tert-butyl-5-chloro-thiazol-2-yl-O-CH₂-CO-N(CH₃)-phenyl) | |
| 81 | (structure: 4-methyl-5-chloro-thiazol-2-yl-O-CH₂-CO-N(CH₃)-phenyl) | |
| 82 | (structure: 4-methyl-5-methoxy-thiazol-2-yl-O-CH₂-CO-N(CH₃)-phenyl) | 160 |

-continued

| Example No. | Formula | Physical data (Refractive index; Melting point °C.) |
|---|---|---|
| 83 | H₃C-C(=N)-C(S)=... -O-CH₂-CO-N(CH₃)-C₆H₅ | |
| 84 | (CH₃)₃C-C(=N)-C(S)=... -O-CH₂-CO-N(CH₃)-C₆H₅ | |
| 85 | H₃C-C(=N)-C(S,C(=O)OCH₃)=... -O-CH₂-CO-N(CH₃)-C₆H₅ | 142 |
| 86 | H₃C-C(=N)-C(S,CH₃)=... -O-CH₂-CO-N(CH₃)-C₆H₅ | 148 |
| 87 | (C₆H₅)-C(=N)-C(S,C₆H₅)=... -O-CH₂-CO-N(CH₃)-C₆H₅ | |
| 88 | H₃C-C(=N)-C(S,S-C₆H₅)=... -O-CH₂-CO-N(CH₃)-C₆H₅ | 63 |
| 89 | H₃C-C(=N)-C(S,OCH₃)=... -O-CH₂-CO-N(CH₃)-C₆H₅ | |
| 90 | H₃C-C(=N)-C(S,C(=O)OC₂H₅)=... -O-CH₂-CO-N(CH₃)-C₆H₅ | |

-continued

| Example No. | Formula | Physical data (Refractive index; Melting point °C.) |
|---|---|---|
| 91 | ![structure: 2-phenyl-thiazole-O-CH2-CO-N(CH3)-phenyl] | |
| 92 | ![structure: 4-methyl-5-cyano-thiazole-O-CH2-CO-N(CH3)-phenyl] | |
| 93 | ![structure with CO-OC2H5 group, H3C, N—S, O-CH2-CO-N(CH3)-phenyl] | |
| 94 | ![4,5-diphenyl-thiazole-O-CH2-CO-N(CH2-CH2-OCH3)2] | 82 |
| 95 | (CH3)2CH-CH(CN)-C(=N-N)-O-C(=N)-O-CH2-CO-N(CH3)-phenyl (1,3,4-oxadiazole) | |
| 96 | phenyl-O-CH2-C(=N-N)-O-C(=N)-O-CH2-CO-N(CH3)-phenyl (1,3,4-oxadiazole) | |
| 97 | (CH3)3C-C(=N-S-N=)-O-CH2-CO-N(CH3)-phenyl (1,2,4-thiadiazole) | $n_D^{23}$: 1.5390 |
| 98 | (CH3)3C-C(=N-S-N=)-O-CH2-CO-N(piperidinyl with 2,6-dimethyl) | 78 |
| 99 | n-C3H7-C(=N-S-N=)-O-CH2-CO-N(CH3)-phenyl | 47 |

-continued
| Example No. | Formula | Physical data (Refractive index; Melting point °C.) |
|---|---|---|
| 100 | 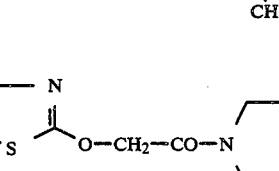 | $n_D^{22}$: 1.4791 |
| 101 | 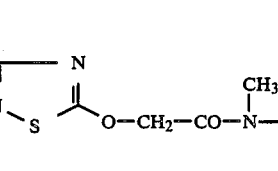 | $n_D^{22}$: 1.5632 |
| 102 | 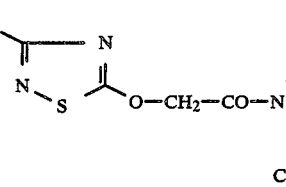 | $n_D^{22}$: 1.5442 |
| 103 | 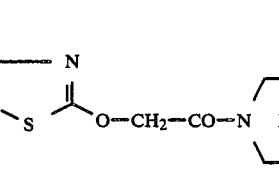 | $n_D^{22}$: 1.4885 |
| 104 | 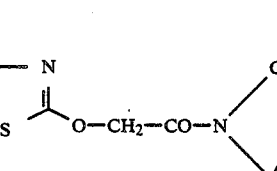 | 87 |
| 105 | 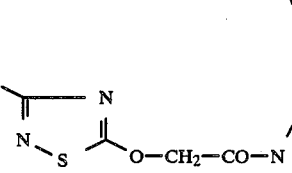 | 84 |
| 106 |  | $n_D^{23}$: 1.5547 |
| 107 | 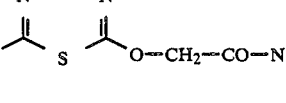 | $n_D^{22}$: 1.5300 |

-continued

| Example No. | Formula | Physical data (Refractive index; Melting point °C.) |
|---|---|---|
| 108 | H₅C₂–C(=N–N=)–S / O–CH₂–CO–N(CH₃)–C₆H₅ (1,3,4-thiadiazole) | $n_D^{22}$: 1.5578 |
| 109 | H₅C₂–C(=N–N=)–S / O–CH₂–CO–N(piperidine-4-spiro-1,3-dioxolane) | $n_D^{22}$: 1.5225 |
| 110 | H₅C₂–C(=N–N=)–S / O–CH₂–CO–N(2,4-dimethylpiperidine) | $n_D^{22}$: 1.5019 |
| 111 | n-C₃H₇S–C(=N–N=)–S / O–CH₂–CO–N(CH₃)–C₆H₅ | $n_D^{22}$: 1.5831 |
| 112 | n-C₃H₇S–C(=N–N=)–S / O–CH₂–CO–N(piperidine-4-spiro-1,3-dioxolane) | $n_D^{22}$: 1.5624 |
| 113 | NH₂–C(=N–O–N=)–C / O–CH₂–CO–N(CH₃)–C₆H₅ (1,2,4-oxadiazole) | $n_D^{22}$: 1.5539 |
| 114 | Cl₂C=C(–N=/–S–)–O–CH₂–CO–N(piperazine)–C₆H₅ | $n_D^{22}$: 1.6102 |
| 115 | Cl₂C=C(–N=/–S–)–O–CH₂–CO–N(piperazine)–C₆H₄–4-F | 60 |
| 116 | Cl₂C=C(–N=/–S–)–O–CH₂–CO–N(piperazine)–N–CH₂–C₆H₅ | $n_D^{22}$: 1.5585 |
| 117 | Cl₂C=C(–N=/–S–)–O–CH₂–CO–N(piperazine)–N–C₆H₄–2-OCH₃ | $n_D^{22}$: 1.5580 |

-continued

| Example No. | Formula | Physical data (Refractive index; Melting point °C.) |
|---|---|---|
| 118 | Cl-C(=N-O-N=)-O-CH₂-CO-N(H)(2-CH₃-piperidine) | 53° |
| 119 | CH₃S-C(=N-S-N=)-O-CH₂-CO-N(CH₃)(2-methyl-5-nitrophenyl) | 190° |
| 120 | Cl-C=C(Cl)-S-C(=N-)-O-CH₂-CO-N(CH₃)(2-methyl-5-nitrophenyl) | 75° |
| 121 | Cl-C(=N-O-N=)-O-CH₂-CO-N(CH₂-CH=CH₂)₂ | $n_D^{20}$: 1.5020 |
| 122 | Cl-C(=N-O-N=)-O-CH₂-CO-N(morpholine) | 86° |
| 123 | Cl-C(=N-O-N=)-O-CH₂-CO-N(piperidine) | 48° |
| 124 | Cl-C(=N-O-N=)-O-CH₂-CO-N(CH₃)₂ | 64° |
| 125 | Cl-C(=N-O-N=)-O-CH₂-CO-N(H)(3-methylpiperidine) | $n_D^{20}$: 1.5052 |
| 126 | Cl-C(=N-O-N=)-O-CH₂-CO-N(C₂H₅)₂ | $n_D^{20}$: 1.4851 |

-continued

| Example No. | Formula | Physical data (Refractive index; Melting point °C.) |
| --- | --- | --- |
| 127 | (4,5-diphenyl-oxazol-2-yl)-O—CH₂—CO—N(n-C₃H₇)(CH(CH₃)CH₂CH₃) | |
| 128 | (4,5-dichloro-thiazol-2-yl)-O—CH₂—CO—N(n-C₃H₇)(CH(CH₃)CH₂CH₃) | |
| 129 | (3-methylthio-1,2,4-thiadiazol-5-yl)-O—CH₂—CO—N(CH₂—CH=CH₂)₂ | $n_D^{21}$: 1.5549 |
| 130 | (3-methyl-1,2,4-thiadiazol-5-yl)-O—CH₂—CO—N(2-methylpiperidinyl) | 68–69° |
| 131 | (3-methylthio-1,2,4-thiadiazol-5-yl)-O—CH₂—CO—N(n-C₃H₇)₂ | $n_D^{21}$: 1.5309 |
| 132 | (4,5-dichloro-thiazol-2-yl)-O—CH₂—CO—N(n-C₃H₇)₂ | $n_D^{21}$: 1.5579 |
| 133 | (4-iso-C₃H₇-1,2,5-thiadiazol-3-yl)-O—CH₂—CO—N(CH₃)(C₆H₅) | 120° |
| 134 | (2-ethylpiperidinyl)-N—CO—CH₂—O-(5-iso-C₃H₇-1,3,4-thiadiazol-2-yl) | 67° |

-continued

| Example No. | Formula | Physical data (Refractive index; Melting point °C.) |
|---|---|---|
| 135 | decahydroquinolin-N—CO—CH₂—O—C(=N—C(C₃H₇-iso))—S—N (thiadiazole) | $n_D^{23}$: 1.5291 |
| 136 | decahydroquinolin-N—CO—CH₂—O—C(S)=N—N=C(C₂H₅) (thiadiazoline) | $n_D^{23}$: 1.5414 |
| 137 | (3,3,5-trimethyl-azepan)-N—CO—CH₂—O—C(=N—C(C₃H₇-iso))—S—N | 75° |
| 138 | (3,3,5-trimethyl-azepan)-N—CO—CH₂—O—C(S)=N—N=C(C₂H₅) | $n_D^{23}$: 1.5212 |
| 139 | (iso-C₃H₇)(C₂H₅)N—CO—CH₂—O—C(S)=N—N=C(C₂H₅) | $n_D^{23}$: 1.5125 |
| 140 | (iso-C₃H₇)(C₂H₅)N—CO—CH₂—O—C(=N—C(C₃H₇-iso))—S—N | 47° |
| 141 | (iso-C₃H₇)(C₂H₅)N—CO—CH₂—O—C(=N—CCl)—S—CCl | $n_D^{23}$: 1.5385 |
| 142 | (2-ethyl-piperidin)-N—CO—CH₂—O—C(S)=N—N=C(C₂H₅) | $n_D^{23}$: 1.5268 |

-continued

| Example No. | Formula | Physical data (Refractive index; Melting point °C.) |
|---|---|---|
| 143 | [structure: 2-methyl-5-ethyl-piperidine-N-CO-CH₂-O-C(=S)-1,3,4-thiadiazole with C₂H₅] | $n_D^{23}$: 1.5172 |
| 144 | [structure: 2-methyl-5-ethyl-piperidine-N-CO-CH₂-O-C(=S)-1,2,4-thiadiazole with iso-C₃H₇] | $n_D^{23}$: 1.4980 |
| 145 | [structure: 2,6-dimethylmorpholine-N-CO-CH₂-O-C(=S)-thiazole with Cl, Cl] | $n_D^{23}$: 1.5559 |
| 146 | [structure: 2-methyl-5-ethyl-piperidine-N-CO-CH₂-O-C(=S)-thiazole with Cl, Cl] | $n_D^{23}$: 1.5371 |
| 147 | [structure: 2,6-dimethylmorpholine-N-CO-CH₂-O-C(=S)-1,3,4-thiadiazole with C₂H₅] | $n_D^{23}$: 1.5367 |
| 148 | [structure: 2,6-dimethylmorpholine-N-CO-CH₂-O-C(=S)-1,2,4-thiadiazole with iso-C₃H₇] | $n_D^{23}$: 1.5162 |
| 149 | [structure: 2,4-dimethylpiperidine-N-CO-CH₂-O-C(=S)-1,3,4-thiadiazole with C(CH₃)₃] | $n_D^{23}$: 1.5162 |
| 150 | [structure: 2-methyl-5-ethyl-piperidine-N-CO-CH₂-O-C(=S)-1,3,4-thiadiazole with C(CH₃)₃] | $n_D^{23}$: 1.5124 |
| 151 | [structure: 2-methylpiperidine-N-CO-CH₂-O-C(=S)-1,3,4-thiadiazole with C(CH₃)₃] | 84–85° |

-continued

| Example No. | Formula | Physical data (Refractive index; Melting point °C.) |
|---|---|---|
| 152 | (structure: 3,3,5-trimethyl-azepane N–CO–CH₂–O–C(=N–N=C(C(CH₃)₃))–S) | $n_D^{23}$: 1.5116 |
| 153 | (structure: 2-ethyl-piperidine N–CO–CH₂–O–C(=N–N=C(C(CH₃)₃))–S) | $n_D^{23}$: 1.5185 |
| 154 | (structure: 1,2,3,4-tetrahydroquinoline N–CO–CH₂–O–C(=N–N=C(C(CH₃)₃))–S) | $n_D^{23}$: 1.5713 |
| 155 | (structure: 1,2,3,4-tetrahydroquinoline N–CO–CH₂–O–C(=N–N=C(C₂H₅))–S) | $n_D^{23}$: 1.5865 |
| 156 | (structure: 1,2,3,4-tetrahydroquinoline N–CO–CH₂–O–C(=N–C(iso-C₃H₇)=N–S)) | $n_D^{23}$: 1.5760 |
| 157 | (structure: iso-C₃H₇O–C(=O)–C=C(CH₃)–N=C(S)–O–CH₂–CO–N(CH₃)(C₆H₅)) | |
| 158 | (structure: Cl₂C=C–S–C(=N)–O–CH₂–CO–N(CH₂–C≡CH)(CH₂–C₆H₅)) | |
| 159 | (n-C₃H₇S–C(=N–N=C(S))–O–CH₂–CO–N(H)(3-methylpiperidine)) | $n_D^{20}$: 1.5461 |

| Example No. | Formula | Physical data (Refractive index; Melting point °C.) |
|---|---|---|
| 160 | CH₃-C(=N-S-N=)-O-CH₂-CO-N(CH₂-CH=CH₂)₂ | $n_D^{20}$: 1.5193 |
| 161 | iso-C₃H₇-C(=N-S-N=)-O-CH₂-CO-N(CH₂-C≡CH)(CH₂-C₆H₅) | |
| 162 | iso-C₃H₇-C(=N-S-N=)-O-CH₂-CO-N(CH₃)(CH₂)₃CH₃ | $n_D^{20}$: 1.4947 |
| 163 | Cl₂C=C(S-N=)-O-CH₂-CO-N(CH₃)(CH₂)₃CH₃ | 47° |
| 164 | iso-C₃H₇-C(=N-S-N=)-O-CH₂-CO-N(C₂H₅)(CH₂)₃CH₃ | |
| 165 | iso-C₃H₇-C(=N-S-N=)-O-CH₂-CO-N(C₂H₅)(C₆H₅) | |
| 166 | Cl₂C=C(S-N=)-O-CH₂-CO-N(C₂H₅)(cyclohexyl) | |
| 167 | Cl₂C=C(S-N=)-O-CH₂-CO-N(C₂H₅)(CH₂)₃CH₃ | |
| 168 | Cl₂C=C(S-N=)-O-CH₂-CO-N(3-methylpiperidinyl) | $n_D^{20}$: 1.5505 |
| 169 | iso-C₃H₇-C(=N-S-N=)-O-CH₂-CO-N(3-methylpiperidinyl) | 45° |
| 170 | iso-C₃H₇-C(=N-S-N=)-O-CH₂-CO-N(3-methylmorpholinyl) | |

-continued
| Example No. | Formula | Physical data (Refractive index; Melting point °C.) |
|---|---|---|
| 171 | 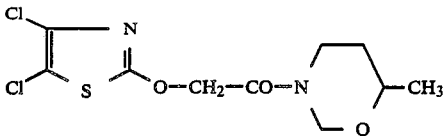 | |
| 172 | 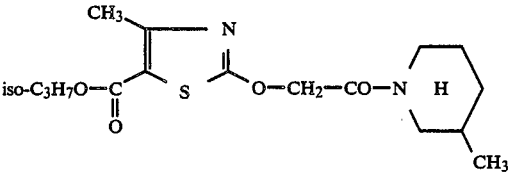 | |
| 173 | 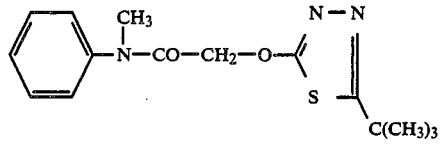 | 85–86° |
| 174 | 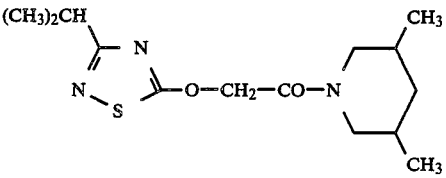 | $n_D^{21}$: 1.5134 |
| 175 | 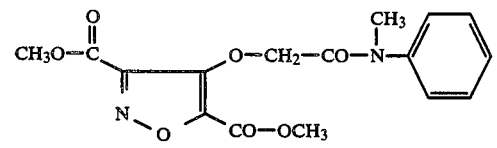 | |
| 176 | 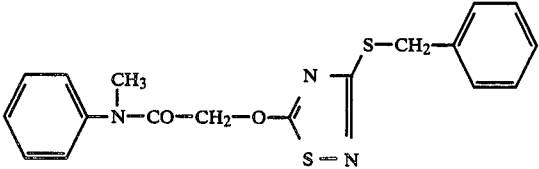 | 108° |
| 177 | 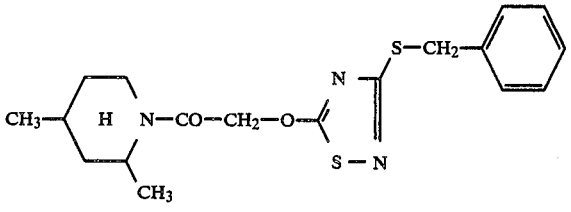 | $n_D^{19}$: 1.5816 |
| 178 | 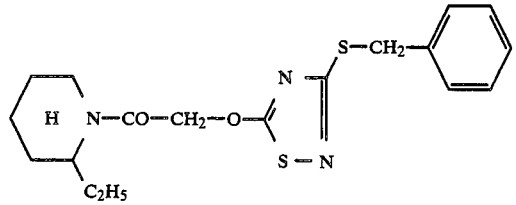 | $n_D^{19}$: 1.5805 |

-continued

| Example No. | Formula | Physical data (Refractive index; Melting point °C.) |
|---|---|---|
| 160 | CH₃-C(=N-N=C(S)-)-O-CH₂-CO-N(CH₂-CH=CH₂)₂ (1,3,4-thiadiazole) | $n_D^{20}$: 1.5193 |
| 161 | iso-C₃H₇-C(=N-N=C(S)-)-O-CH₂-CO-N(CH₂-C≡CH)(CH₂-C₆H₅) | |
| 162 | iso-C₃H₇-C(=N-N=C(S)-)-O-CH₂-CO-N(CH₃)((CH₂)₃CH₃) | $n_D^{20}$: 1.4947 |
| 163 | Cl₂C=C(-N=C(S)-)-O-CH₂-CO-N(CH₃)((CH₂)₃CH₃) | 47° |
| 164 | iso-C₃H₇-C(=N-N=C(S)-)-O-CH₂-CO-N(C₂H₅)((CH₂)₃CH₃) | |
| 165 | iso-C₃H₇-C(=N-N=C(S)-)-O-CH₂-CO-N(C₂H₅)(C₆H₅) | |
| 166 | Cl₂C=C(-N=C(S)-)-O-CH₂-CO-N(C₂H₅)(cyclohexyl) | |
| 167 | Cl₂C=C(-N=C(S)-)-O-CH₂-CO-N(C₂H₅)((CH₂)₃CH₃) | |
| 168 | Cl₂C=C(-N=C(S)-)-O-CH₂-CO-N(3-methylpiperidinyl) | $n_D^{20}$: 1.5505 |
| 169 | iso-C₃H₇-C(=N-N=C(S)-)-O-CH₂-CO-N(3-methylpiperidinyl) | 45° |
| 170 | iso-C₃H₇-C(=N-N=C(S)-)-O-CH₂-CO-N(2-methylmorpholinyl) | |

-continued

| Example No. | Formula | Physical data (Refractive index; Melting point °C.) |
|---|---|---|
| 171 | (structure with Cl, Cl, S, N, O—CH₂—CO—N, morpholine ring with CH₃) | |
| 172 | (structure with CH₃, iso-C₃H₇O—C(=O), S, N, O—CH₂—CO—N, piperidine with CH₃) | |
| 173 | (phenyl-N(CH₃)-CO-CH₂-O-C(=N-N=C(CH₃)₃)-S) | 85–86° |
| 174 | ((CH₃)₂CH, N, S, N, O—CH₂—CO—N, piperidine with two CH₃) | $n_D^{21}$: 1.5134 |
| 175 | (CH₃O-C(=O), isoxazole with N-O, CO-OCH₃, O—CH₂—CO—N(CH₃)-phenyl) | |
| 176 | (phenyl-N(CH₃)-CO-CH₂-O-C(=N)(S-CH₂-phenyl)-S-N) | 108° |
| 177 | (CH₃, piperidine with CH₃, N-CO-CH₂-O-C(=N)(S-CH₂-phenyl)-S-N) | $n_D^{19}$: 1.5816 |
| 178 | (piperidine with C₂H₅, N-CO-CH₂-O-C(=N)(S-CH₂-phenyl)-S-N) | $n_D^{19}$: 1.5805 |

-continued
| Example No. | Formula | Physical data (Refractive index; Melting point °C.) |
|---|---|---|
| 195 | 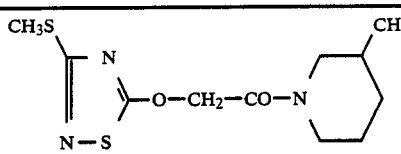 | 71° |
| 196 | 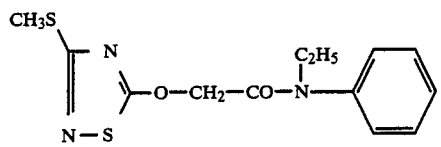 | 118° |
| 197 | 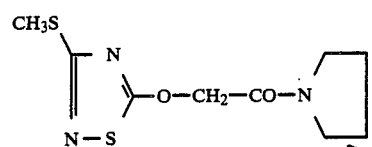 | |
| 198 | 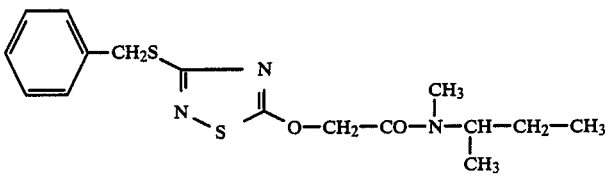 | |
| 199 | 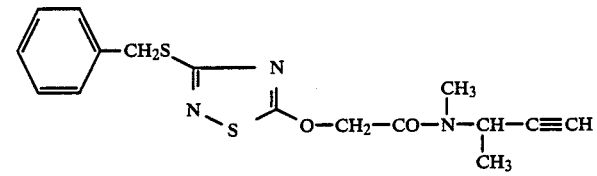 | |
| 200 | 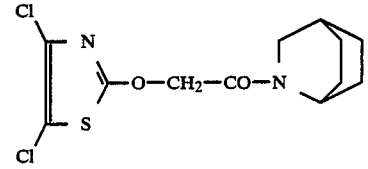 | |
| 201 | 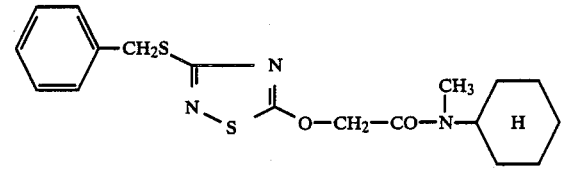 | |
| 202 | 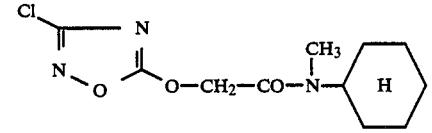 | |
| 203 | 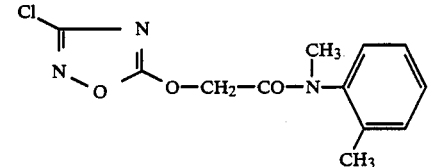 | |

-continued

| Example No. | Formula | Physical data (Refractive index; Melting point °C.) |
|---|---|---|
| 204 | Cl–C(=N–O–N)–O–CH₂–CO–N(C₂H₅)(cyclohexyl), H | |
| 205 | Cl–C(=N–O–N)–O–CH₂–CO–N(CH₃)–CH(CH₃)–C≡CH | |
| 206 | Cl–C(=N–O–N)–O–CH₂–CO–N(CH₃)–CH(CH₃)–CH₂–CH₃ | |
| 207 | 4-CH₃,2-CH₃-piperidin-N–CO–CH₂–O–C(=N–N=C(SC₄H₉-n))S | $n_D^{23}$: 1.5550 |
| 208 | 2-CH₃-piperidin-N–CO–CH₂–O–C(=N–N=C(SC₄H₉-n))S | $n_D^{23}$: 1.5738 |
| 209 | 4-C₂H₅-piperidin-N–CO–CH₂–O–C(=N, S–N)(S–CH₂–C₆H₅) | 138° |
| 210 | CH₃–C(=N–N=S)–O–CH₂–CO–N(azepan), H | $n_D^{20}$: 1.5130 |
| 211 | CH₃–C(=N–N=S)–O–CH₂–CO–N(CH₃)₂ | 110° |
| 212 | CH₃–C(=N–N=S)–O–CH₂–CO–N(C₂H₅)₂ | $n_D^{20}$: 1.5130 |
| 213 | iso-C₃H₇–C(=N–N=S)–O–CH₂–CO–N(3-CH₃-piperidin), H | 45° |

-continued

| Example No. | Formula | Physical data (Refractive index; Melting point °C.) |
|---|---|---|
| 214 | C₆H₅—CH₂—S—C(=N—)—N=S— (1,2,4-thiadiazole), 3-position —O—CH₂—CO—N(H)—(3-methylpiperidinyl) | 119° |
| 215 | C₆H₅—CH₂—S—C(=N—)—N=S— (1,2,4-thiadiazole), 3-position —O—CH₂—CO—N(H)—(4-methylpiperidinyl) | 128° |
| 216 | H₃C—C(=N—)—C(S—)(CO—O—iso-C₃H₇); —O—CH₂—CO—N(CH₃)—C₄H₉-iso | |
| 217 | H₃C—C(=N—)—C(S—)(CO—O—iso-C₃H₇); —O—CH₂—CO—N(CH₃)—(2-methylphenyl)(CH₃) | |
| 218 | Cl—C(=N—)=C(Cl)(S—); —O—CH₂—CO—N(CH₃)—CH₂—(2-methyltetrahydrofuran-2-yl) | |
| 219 | iso-C₃H₇—C(=N—)—N=S— (1,2,4-thiadiazole); —O—CH₂—CO—N(CH₃)—CH₂—(2-methyltetrahydrofuran-2-yl) | |
| 220 | C₆H₅—CH₂—S—C(=N—)—N=S—; —O—CH₂—CO—N(C₂H₅)—cyclohexyl | |
| 221 | C₆H₅—CH₂—S—C(=N—)—N=S—; —O—CH₂—CO—N—(2,6-dimethylmorpholinyl) | |

| Example No. | Formula | Physical data (Refractive index; Melting point °C.) |
|---|---|---|
| 222 | (structure: benzyl-CH₂-S-C(=N-S-N=)-O-CH₂-CO-N(CH₃)(o-tolyl)) thiadiazole with CH₂-S-benzyl substituent; O-CH₂-CO-N(CH₃)-(2-methylphenyl) | |
| 223 | thiadiazole with CH₂-S-benzyl; O-CH₂-CO-N(CH₂-CH=CH₂)₂ | 54° |
| 224 | thiadiazole with isoC₃H₇; O-CH₂-CO-N(hexamethyleneimine, H label) | 60° |
| 225 | thiadiazole with 4-CF₃-phenyl; O-CH₂-CO-N(CH₃)(phenyl) | |
| 226 | thiadiazole with 3-CF₃-phenyl; O-CH₂-CO-N(CH₃)(phenyl) | |
| 227 | thiadiazole with CH₃S; O-CH₂-CO-N(CH₃)(2-fluorophenyl) | |
| 228 | thiadiazole with CH₃S; O-CH₂-CO-N(CH₃)(3-fluorophenyl) | |
| 229 | thiadiazole with n-C₃H₇; O-CH₂-CO-N(CH₃)(4-fluorophenyl) | |
| 230 | 1,3,4-thiadiazole with phenyl; O-CH₂-CO-N(CH₃)(3-CF₃-phenyl) | |

-continued

| Example No. | Formula | Physical data (Refractive index; Melting point °C.) |
|---|---|---|
| 231 | 4-CF₃-C₆H₄-C(=N-N=)-S-C(-)-O-CH₂-CO-N(CH₃)-C₆H₅ | |
| 232 | 2-CF₃-C₆H₄-C(=N-N=)-S-C(-)-O-CH₂-CO-N(CH₃)-C₆H₅ | |
| 233 | 3-CF₃-C₆H₄-C(=N-N=)-S-C(-)-O-CH₂-CO-N(CH₃)-C₆H₅ | |
| 234 | CH₃-C(=N-)-S-N=C(-)-O-CH₂-CO-N(C₂H₅)-(2-Cl-C₆H₄) | |
| 235 | 4,5-diCl-thiazol-2-yl-O-CH₂-CO-N(CH₃)-(3-Cl-C₆H₄) | |
| 236 | 4,5-diCl-thiazol-2-yl-O-CH₂-CO-N(CH₃)-(4-Cl-C₆H₄) | |
| 237 | CH₃S-C(=N-)-S-N=C(-)-O-CH₂-CO-N(CH₃)-(2,4-diCl-C₆H₃) | |
| 238 | Cl-C(=N-)-O-N=C(-)-O-CH₂-CO-N(CH₃)-(3-CH₃-C₆H₄) | |
| 239 | Cl-C(=N-)-O-N=C(-)-O-CH₂-CO-N(CH₃)-(4-CH₃-C₆H₄) | |

-continued

| Example No. | Formula | Physical data (Refractive index; Melting point °C.) |
|---|---|---|
| 240 | iso-C₃H₇ group on thiadiazole, -O-CH₂-CO-N(CH₃)-(2,4-dimethylphenyl) | |
| 241 | CH₃S group on thiadiazole, -O-CH₂-CO-N(CH₃)-(2-CF₃-phenyl) | |
| 242 | H₃C group on thiadiazole, -O-CH₂-CO-N(CH₃)-(3-CF₃-phenyl) | |
| 243 | iso-C₃H₇ group on thiadiazole, -O-CH₂-CO-N(CH₃)-(4-CF₃-phenyl) | |
| 244 | Cl group on oxadiazole (N—O), -O-CH₂-CO-N(CH₃)-(3,5-bis-CF₃-phenyl) | |
| 245 | phenyl-thiadiazole (N=N,S), -O-CH₂-CO-N(CH₃)-(2-OCH₃-phenyl) | |
| 246 | n-C₃H₇-SO₂ thiadiazole (N=N,S), -O-CH₂-CO-N(CH₃)-(3-OCH₃-phenyl) | |
| 247 | CH₃S group on thiadiazole, -O-CH₂-CO-N(CH₃)-(4-OCH₃-phenyl) | |
| 248 | 2,4,6-trimethylpiperidine-N-CO-CH₂-O-benzoxazole | $n_D^{21}$: 1.5298 |

The compounds of the formula (II) to be used as starting substances could be prepared, for example, as follows:

Example a

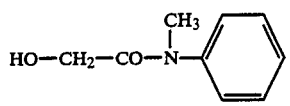

A suspension of 183.5 g (1 mol) of chloroacetic acid N-methylanilide, 82 g (1 mol) of anhydrous sodium acetate and 320 ml of toluene was heated to 115°–120° C. for 4 hours and then cooled to room temperature. The batch was filtered and the residue was rinsed with cold toluene. After distilling off the solvent from the toluene solution and evaporating the residue in a steam jet vacuum at a bath temperature of 80°–85° C., 207 g of α-acetoxy-acetic acid N-methylanilide, which crystallised on standing, were obtained. GC [GC=according to the gas chromatogram]=98% pure; melting point: 54°–56° C.; yield: 99% of theory.

A reaction mixture of 211.2 g (1 mol) of α-acetoxyacetic acid N-methylanilide (98% pure), 0.2 g of sodium hydroxide and 160 g of methanol was heated under reflux for 4 hours. The mixture of methanol and methyl acetate was distilled off. The liquid distillation residue [170 g yield of hydroxy-acetic acid N-methylanilide, quantitative; GC: 98%; melting point: 52°–53° C.] solidified on cooling.

The compounds of the formula

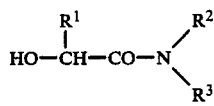

below were obtained analogously:

TABLE 2

| Example | R$^1$ | —N(R$^2$)(R$^3$) | Melting point (°C.); Refractive index; |
|---|---|---|---|
| b | H | (N-methylpiperidinyl structure) | 36 |
| c | H | —N(CH$_2$—CH$_2$—OCH$_3$)$_2$ | n$_D^{25}$ :1,4662 |
| d | H | (N-methylcyclohexylamino structure) | 83 |
| e | H | —N(CH$_3$)—CH(CH$_3$)—C≡CH | n$_D^{25}$ :1,4859 |

TABLE 2-continued

| Example | R$^1$ | —N(R$^2$)(R$^3$) | Melting point (°C.); Refractive index; |
|---|---|---|---|
| f | H | (2,6-dimethylpiperidinyl structure) | n$_D^{23}$ :1,4816 |
| g | H | (decahydroquinolinyl structure) | 55 |
| h | H | (tetrahydroquinolinyl-like structure) | n$_D^{23}$ :1,5076 |
| i | H | (tetrahydroquinolinyl structure) | 80 |
| j | H | (methyl-decahydroquinolinyl structure) | — |

It will be understood that the specification and examples are illustrative but not limitative of the present invention and that other embodiments within the spirit and scope of the invention will suggest themselves to those skilled in the art.

What is claimed is:

1. An herbicidal composition comprising an herbicidally acceptable carrier and, in herbicidally effective amounts, an azolyloxy-carboxylic acid amide compound of the formula

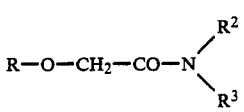

wherein

R is selected from the group consisting of the following azolyl radicals:

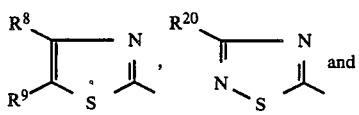 

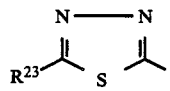

$R^2$ is hydrogen or $C_1$–$C_5$-alkyl, $R^3$ is a $C_1$–$C_5$-alkyl, phenyl, or phenyl substituted 1 to 3 times by methyl, fluorine, chlorine, trifluoromethyl, cyano, nitro or methoxy, and $R^8$, $R^9$, $R^{20}$ and $R^{23}$ which can be identical or different, individually represent hydrogen, chlorine, bromine, $C_1$–$C_4$-alkylsuphonyl, or halogen substituted $C_1$–$C_6$-alkyl.

2. The composition of claim 1 wherein said halogen substituted $C_1$–$C_6$ alkyl is a chloro, fluoro, or chloro and fluorosubstituted $C_1$–$C_6$ alkyl.

3. The composition of claim 1 wherein the $C_1$–$C_5$ alkyl of $R_2$ and $R_3$ is methyl.

4. The composition of claim 1 wherein at least one of $R^8$, $R^9$, $R^{20}$ and $R^{23}$ is fluoromethyl, chloromethyl, fluorochloromethyl, difluoromethyl, dichloromethyl, trifluoromethyl, trichloromethyl, difluorochloromethyl or fluorodichloromethyl.

5. The herbicidal composition of claim 1 wherein $R^2$ is $C_1$–$C_5$-alkyl, $R^3$ is phenyl or phenyl substituted 1 to 3 times by methyl, fluorine, chlorine, trifuoromethyl, cyano, nitro or methoxy and R is

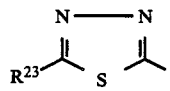

in which $R^{23}$ is $C_1$–$C_4$ alkylsulphonyl.

6. The composition of claim 5 wherein $R^3$ is phenyl.

7. An herbicidal composition comprising an herbicidally acceptable carrier and, in an herbicidally effective amount, O-(2-methylsulphonyl-1,3,4-thiadiazol-5-yl)oxyacetic acid N-methylanilide.

8. A method of combating weeds which method comprises applying to the weeds or their habitat a herbicidally effective amount of an azolyoxy-carboxylic acid amide compound of the formula

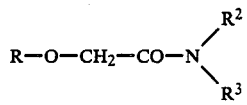

wherein

R is selected from the group consisting of the following azolyl radicals:

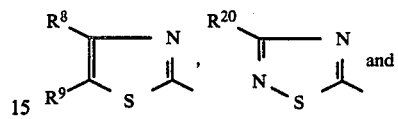

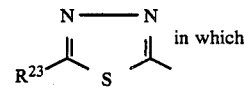

$R^2$ is hydrogen or $C_1$–$C_5$-alkyl, $R^3$ is $C_1$–$C_5$-alkyl, phenyl, or phenyl substituted 1 to 3 times by methyl, fluorine, chlorine, trifluoromethyl, cyano, nitro or methoxy, and $R^8$, $R^9$, $R^{20}$ and $R^{23}$ which can be identical or different, individually represent hydrogen, chlorine, bromine, $C_1$–$C_4$-alkylsuphonyl, or halogen substituted $C_1$–$C_6$-alkyl.

9. Method as claimed in claim 8 wherein said azolyloxy-carboxylic acid amide compound is selected from
O-(4,5-dichloro-1,3-thiazol-2-yl)oxyacetic acid N-methylanilide, and
O-(4,5-dichloro-1,3-thiazol-2-yl)oxyacetic acid N-dimethylamide.

10. Method as claimed in claim 8 wherein said compound is applied at a dosage of 0.01 to 10 kg per hectare.

11. Method as claimed in claim 10 wherein said compound is applied at a dosage of 0.01 to 5 kg per hectare.

12. The method of claim 8 wherein said halogen substituted $C_1$–$C_6$ alkyl is a chloro, fluoro, or chloro and fluorosubstituted $C_1$–$C_6$ alkyl.

13. The method of claim 8 wherein the $C_1$–$C_5$ alkyl or $R_2$ and $R_3$ is methyl.

14. The method of claim 8 wherein at least one of $R^8$, $R^9$, $R^{20}$ and $R^{23}$ is fluoromethyl, chloromethyl, fluorochloromethyl, difluoromethyl, dichloromethyl, trifluoromethyl, trichloromethyl, difluorochloromethyl or fluorodichloromethyl.

15. A method of combating weeds comprising applying to the weeds, or their habitat, an herbicidally effective amount of the composition of claim 7.

* * * * *